United States Patent
Persson et al.

(10) Patent No.: US 6,310,042 B1
(45) Date of Patent: *Oct. 30, 2001

(54) DERIVATIVES OF CARBOHYDRATES AND COMPOSITIONS CONTAINING THEM

(76) Inventors: Lars Persson, Mollegangen 17, S-281 37 Hassleholm; Nicola Rehnberg, Klovergaten 28, S-284 00 Perstorp, both of (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/196,743

(22) Filed: Nov. 20, 1998

Related U.S. Application Data

(63) Continuation of application No. 08/809,169, filed as application No. PCT/SE95/01044 on Sep. 15, 1995, now abandoned.

(30) Foreign Application Priority Data

Sep. 20, 1994 (SE) ................................. 9403137

(51) Int. Cl.[7] ............... A61K 31/70; C07H 13/00; C07H 11/04
(52) U.S. Cl. ................ 514/23; 514/25; 536/4.1; 536/17.1; 536/18.5; 536/18.6; 536/117; 536/120
(58) Field of Search .................. 514/23, 25; 536/4.1, 536/17.1, 18.5, 18.6, 117, 120

(56) References Cited

U.S. PATENT DOCUMENTS 3,652,743 * 3/1972 Harris et al. .

FOREIGN PATENT DOCUMENTS

| 0456948 | 11/1991 | (EP) . |
| 2019839 * | 7/2001 | (ES) . |
| 1158962 | 7/1969 | (GB) . |
| 1429592 * | 8/1988 | (SU) . |
| 9001938 | 3/1990 | (WO) . |
| 9118022 * | 11/1991 | (WO) . |
| 9328777 | 9/1993 | (WO) . |

OTHER PUBLICATIONS

Camilleri et al., J. Chem. Soc. Perkin Trans. 2, vol. 10: 2085–90, (1994).*

Kirby et al., J. Chem. Soc. Chem. Commun., vol. 6: 709–710, (1994).*

Caro et al., Carbohydrate Res., vol. 240: 119–131, (1993).*

Chung et al., Korean J. Med. Chem., vol. 2(2): 131–8, (1992).*

Chung et al., J. Chem. Soc., Chem. Commun., vol. 1: 77–79, (1992).*

Chung et al., Carbohydrate Res., vol. 260(1): 39–50, (1994).*

CA, vol. 118, No. 21, May 24, 1993, Abstract No. 213365.

CA, vol. 114, No. 3, Jan. 21, 1991, Abstract No. 24352.

* cited by examiner

*Primary Examiner*—Kathleen Kahler Fonda
*Assistant Examiner*—Leigh C. Maier
(74) *Attorney, Agent, or Firm*—Stevens, Davis, Miller & Mosher, L.L.P.

(57) ABSTRACT

The present invention relates to derivatives of phosphorylated carbohydrates and pharmaceutical compositions comprising as a pharmaceutically active ingredient at least one of these compounds.

7 Claims, No Drawings

DERIVATIVES OF CARBOHYDRATES AND COMPOSITIONS CONTAINING THEM

CROSS REFERENCE TO RELATED APPLICATIONS

This application is a continuation of application Ser. No. 08/809,169, filed Mar. 13, 1997 now abondoned; which is a 35 USC § 371 application of International Application PCT/SE95/01044 filed Sep. 15, 1995.

The present invention relates to derivatives of phosphorylated carbohydrates and pharmaceutical compositions comprising as a pharmaceutically active ingredient at least one of these compounds.

Some phosphorylated carbohydrates exist in mammals and are considered to have specific biological properties. Lyscsomes contain a large amount of degradative enzymes which play a role in the entry of cells such as leukocytes into inflammatory areas. These enzymes undergo glycosylation and phosphorylation resulting in residues containing mannose-monophosphates. Thus it has been shown that the administration of mannose-6-phosphate to animals suffering from adjuvant arthritis reduces the inflammatory expression (PCT Patent Application publication WO 90/01938) to some extent.

Furthermore it has been shown that mannose-6-phosphate might promote wound healing when given to animals (PCT Patent Application publication WO 93/18777).

Other monophosphorylated carbohydrates also occur in a living organism. An example is the formation of glucose-1-phosphnate and glucose-6-phosphate after the cleavage of glycogen rendering an energy-rich structure.

The utilization of phosphorylated carbohydrates for preparing pharmaceutical compositions has been very limited for many reasons. Monophosphorylated carbohydrates exhibit low potency when applied in animal models which results in the need of fairly large amounts administered which would not be beneficial in a patient situation. Furthermore high dosages expose the risk of side effects and lack of selectivity regarding the therapeutic effect. These type of compounds also have a very short half life due to the fast enzymatic degradation by for example alkaline phosphatases.

According to the present invention it has quite unexpectedly been possible to produce novel derivatives of phosphorylated carbohydrates in substantially pure form.

The invention relates to compounds of formula (I)

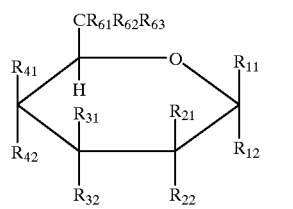

(I)

where three of $R_{11}/R_{12}$, $R_{21}/R_{22}$, $R_{31}/R_{32}$, $R_{41}/R_{42}$ and $R_{61}/R_{62}/R_{63}$ are

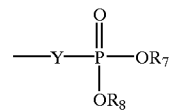

where Y is
(1) oxygen
(2) $(CH_2)_n$, where n is 1–4
(3) $(-CH_2-)_nO$ where n is 1–4
and where $R_7$ and $R_8$ independently are
(1) hydrogen
(2) a cation selected from the group of sodium, potassium, calcium, magnesium and zinc
(3) an alkyl or substituted alkyl selected from the group of methyl, ethyl, propyl, butyl, pentyl, hexyl, heptyl, octyl, nonyl, decyl, undecyl, dodecyl, tridecyl, tetradecyl or pentadecyl
(4) an aryl or substituted aryl selected from the group of phenyl, biphenyl, terphenyl or naphcyl or
(5) an acyl or substituted acyl selected from the group of formyl, acetyl, propionyl, butyryl, isobutyryl, valeryl, isovaleryl, pivaloyl, lauroyl, myristoyl, palmitoyl, stearoyl, oxalyl, malonyl, succinyl, glutaryl, glyceryl, benzoyl, cinnamoyl and nico inyl where four of $R_{11}/R_{12}$, $R_{21}/R_{22}$, $R_{31}/_{32}$ and $R_{41}/R_{42}$ are hydrogen and where the remaining of $R_{11}$, $R_{12}$, $R_{21}$, $R_{22}$, $R_{31}$, $R_{32}$, $R_{41}$, $R42$, $R_{61}$, $R_{62}$ and $R_{63}$ are
(1) hydrogen
(2) $-OR_9$
where $R_9$ is
(a) straight or branched alkyl with 1 to 24 carbon atoms
(b) cycloalkyl with 3 to 16 carbon atoms
(c) alkenyl with 2 to 24 carbon atoms
(d) cycloalkenyly with 4 to 16 carbon atoms
(e) aryl with 6 to 24 carbon atoms
(f) aralkyl
(g) alkaryl
(h) aralkenyl
(i) alkenylaryl
(j) a heterocyclic group with at least one carbon of oxygen, nitrogen or sulfur
(k) a glycosyl residue
(l) a glycopeptide
(m) a glycoprotein
(n) a glycolipid
(o) carboxy, sulfonyl or phosphonyl
(p) silyl or substituted silyl
(q) hydrogen
the above groups (a) to (n) are unsubstituted or substituted with hydroxy, oxo, alkoxy, aryloxy, halo, cyano, isocyanato, carboxy, esterified carboxy, amino, substituted amino, formyl, acyl, acyloxy, acylamino, sulfinyl, sulfonyl, phosphino, phosphinyl, phosphonyl, mercapto, alkylthio, arylthio, silyl, silyloxy, silylthio, nitro or azido

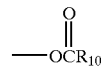

(3)

where $R_{10}$ is
(a) straight or branched alkyl with 1 to 24 carbon atoms (b) cycloalkyl with 3 to 16 carbon atoms
(c) alkenyl with 2 to 24 carbon atoms
(d) cycloalkenyl with 4 to 16 carbon atoms
(e) aryl with 6 to 24 carbon atoms
(f) aralkyl
(g) alkaryl
(h) aralkenyl
(i) alkenylaryl
(j) a heterocyclic group with at least one carbon of oxygen, nitrogen or sulfur
(k) carboxy or esterified carboxy
(l) amino or substituted amino or
(m) hydrogen
the above groups (a) to (i) are unsubstituted or substituted with hydroxy, oxo, alkoxy, aryloxy, halo, cyano, isocyanato, carboxy, esterified carboxy, amino, substituted amino, formyl, acyl, acyloxy, acylamino, sulfinyl, sulfonyl, phosphino, phosphinyl, phosphonyl, mercapto, alkylthio, arylthio, silyl, silyloxy, silylthio, nitro or azido or
(4) —$NR_{13}R_{14}$ where $R_{13}$ and $R_{14}$ independently are
(a) hydrogen
(b) hydroxyl
(c) acyl or substituted acyl selected from the group of formyl, acetyl, propionyl, butyryl, isobutyryl, valeryl, isovaleryl, pivaloyl, lauroyl, myristoyl, palmitoyl, stearoyl, oxalyl, malonyl, succinyl, glutaryl, benzoyl, cinnamoyl or nicotinoyl
(d) alkyl or substituted alkyl selected from the group of methyl, ethyl, propyl, butyl, pentyl, hexyl, heptyl, octyl, nonyl, decyl, undecyl, dodecyl, tridecyl, tetradecyl or pentadecyl or
(e) aryl or substituted aryl selected from the group of phenyl, biphenyl, terphenyl or naphtyl The expression $R_{11}/R_{12}$ etc above or generally ($R_n/R_{n+1}$) means that only one of Rn and $R_{n+1}$ could be the radical described i.e. if $R_n$ is

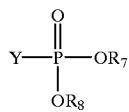

$R_{n+1}$ could not be the same in one specific compound.

According to the invention three of $R_{11}/R_{12}$, $R_{21}/R_{22}$, $R_{31}/R_{32}$, $R_{41}/R_{42}$ and $R_{61}/R_{62}/R_{63}$ are

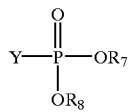

where Y is oxygen or $(CH_2—)_n$
or $(—CH_2—)_nO$; n=1–4.

In one preferred form Y is oxygen which means that three of $R_{11}/R_{12}$, R21/R22, $R_{31}/R_{32}$, $R_{41}/R_{42}$ and $R_{61}/R_{62}/R_{63}$ are

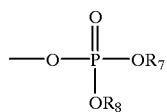

$R_7$ and $R_8$ can independently be hydrogen, a cation, alkyl or substituted alkyl, aryl or substituted aryl or acyl or substituted acyl. Preferably $R_7$ and $R_8$ are hydrogen, a cation or a lower alkyl such as methyl, ethyl, propyl, butyl or pentyl.

The radicals $R_9$ and $R_{10}$ above can be an alkyl with 1 to 24 carbon atoms, for example, lower alkyl such as methyl, ethyl, n-propyl, isopropyl, n-butyl, tributyl, sec.-butyl or tert.-butyl, also n-pentyl, neo-pentyl, n-hexyl or n-heptyl or higher alkyl such as straight-chain or branched octyl, nonyl, decyl, undecyl, dodecyl, tridecyl, tetradecyl, pentadecyl, hexadecyl, heptadecyl, octadecyl, nonadecyl, eicosyl, docosyl and n-tetracosyl;

Cycloalkyl with 3 to 16 carbon atoms is, for example, cyclopropyl, cyclobutyl, cyclopentyl, cyclohexyl, cycloheptyl, cyclooctyl, cyclononyl and adamantyl;

Alkenyl with 2 to 24 carbon atoms is, for example, lower alkenyl such as vinyl, allyl, propenyl, butenyl, pentenyl and hexenyl or higher alkenyl such as oczadienyl, octenyl, decenyl, dodecenyl, tetradecenyl, hexadecenyl, octadecenyl, octadecadienyl, octadecatrienyl, nonadecenyl and arachidonyl;

Cycloalkenyl with 4 to 16 carbon atoms is, for example, cyclobutenyl, cyclopentenyl, cyclohexenyl, cyclohexadienyl, cycloheptenyl, cyclooctenyl, cyclooctadienyl and cyclooctatrienyl;

Aryl with 6 to 24 carbon atoms is, for example, phenyl, biphenyl, terphenyl, naphtyl, anthracenyl, phenanthrenyl;

The radicals $R_9$ and $R_{10}$ an also be a heterocyclic group containing at least one atom selected from the group of oxygen, nitrogen and sulphur and is for example pyridylt pyrrolyl, pyrrolidinyl, piperidinyl, indolyl, imidazolyl, furyl, dioxolanyl, cxiranyl, thiiranyl, thiopyranyl, oxazolyl and thiazoiyl.

$R_9$ can also be an etherified hydroxyl with a carbon radical which is a glycosyl residue. The glycosyl residue is derived for example from a monosaccharide such as erythrose, ribose, arabinose, allose, altrose, glucose, mannose, threose, xylose, lyxose, gulose, idose, galactose, talose, fructose or from a polysaccharide such as maltosed lactose, cellobiose or sucrose or nonhydrolyzed or partially hydrolyzed cellulose, amylose or amylopectin.

Preferably the glycosyl residue is derived from glucose, fructose, mannose or lactose.

The glycosyl residue could also be substituted with for example carboxyl, amino- or phosphonyl groups such as glucoseamine or galactoseamine or glucosephosphate or glucopyranosyl phosphate or sialic acid.

$R_9$ can also be an etherified hydroxyl with a carbon radical which is a glycopeptide. This radical is derived for example from one or more sugar residues which are attached primarily to serine, threonine or aspargine side chains of the peptide, where the peptide is formed by different combinations of amino acids up to a molecular weight of 10.000. Prefered radicals are those which include glucoseamine or galactoseamine attached to especially di- and tripeptides.

$R_9$ can also be an etherified hydroxyl with a carbon radical which is a glycoprotein. This radical is derived for example from one or more sugar residues which are attached primarily to serine, threonine or aspargine side chains of the proteins, especially alkaline phosphatase, acetyrcholinesterase, 5-nucleotidase. Thy-1, Th B and Heparan sulphate proteoglycan. Preferred radicals are those which include glucoseamine and galactoseamine attached to the protein. Especially preferred radicals are lectins such as concanavalin A, wheat germ agglutinin, peanutagglutinin and seromucoid and orosomucoid.

$R_9$ can also be an etherified hydroxyl with a carbon radical which is glycolipid. This radical is derived for example from one or more sugar residues which are attached to a lipid.

Preferred radicals are those which include glucose or galactose. Further preferred radicals are cerebroside and ganglioside.

$R_9$ can also be a functional group such as carboxyl, phosphonyl or sulfonyl.

$R_9$ can also be a silyl or substituted silyl such alkyl silyl or arylsilyl.

The above mentioned radicals on $R_9$ and $R_{10}$ are unsubstituted or substituted.

The substitution could consist of free functional groups such as hydroxyl, carbonyl, carboxyl, mercapto or amino or these groups could be present in protected form.

Thus, carboxyl groups are usually protected in esterified form and contain as esterifying groups especially lower alkyl groups, which could be branched in the 1-position or suitably substituted in the 1- or 2-position. Preferred carboxyl groups protected in esterified form are for example methoxycarbonyl, butoxycarbonyl, tert. alkoxycarbonyl such as tert. butoxycarbonyl or arylmethoxycarbonyl having one or two aryl radicals. These aryl radicals preferably consist of phenyl radicals optionally substituted for example by lower alkyl, lower alkoxy, hydroxy, halogen and/or nitro, such as benzyloxycarbonyl, methoxybenzyloxycarbonyl, diphenylmethoxycarbonyl, 2-bromoethoxycarbonyl or 2-iodo-ethoxycarbonyl. Other preferred protected carboxyl groups in esterified form are silyloxycarbonyl groups, especially organic silyloxycarbonyl groups. In these the silicon atom preferably contains as substituent a lower alkyl, especially methyl, or alkoxy, especially methoxy and/or halogen, for example chlorine. Suitable silyl-protecting groups are for example trimethylsilyl and dimethyl-tert.-butylsilyl.

A protected amino group may be present for example, in the form of an acylamino group or in the form of arylalkyl amino group or azido group or sulphonated amino group. In a corresponding acylamino group the acyl is for example the acyl radical of an organic carboxylic acid having for example up to 18 carbon atoms, especially the acyl radical of an alkanecarboxylic acid which is preferably substituted with halogen or aryl or of a carboxylic acid semiester.

Such acyl groups are for example lower alkanoyl such as formyl or acetyl; halo-lower alkanoyl such as 2-chloro-and 2-bromoacetyl or lower alkoxycarbonyl straight or branched in the 1-position of the lower alkyl radical or suitably substituted in the 1- or 2-position, for example tert. butyl carbonyl; arylmethoxycarbonyl having one or two aryl radicals which are unsubstituted or, in the case of phenyl, may be substituted for example with lower alkyl, especially tert. lower alkyl, lower alkoxy, hydroxy, halogen and/or nitro; such as unsubstituted or substituted aryloxycarbonyl, for example benzyloxycarbonyl or 4-nitro-benzyloxycarbonyl or diphenylmethoxycarbonyl, for example benzhydroxycarbonyl or di-(4-methoxyphenyl)-methoxycarbonyl; aroylmethoxycarbonyl for example phenacyloxycarbonyl in which the aroyl group is benzoyl which is unsubstituted or substituted for example with halogen; halo-lower alkoxycarbonyl, for example 2-bromo- or 2-iodoethoxycarbonyl; or 2-(trisubstituted silyl)-ethoxycarbonyl such as for example 2-trimethylsilylethoxycarbonyl or 2-triphenylsilylethoxycarbonyl.

An arylalkylamino group is a mono-, di- or especially a triarylalkylamino group in which the aryl radicals are especially unsubstituted or substituted phenyl radicals. Such groups are for example benzylamino, diphenylmethylamino or tritylamino.

Amino groups may also contain organic silyl groups as protecting groups. Suitable silylprotecting groups are especially tri-lower alkylsilyl, such as trimethylsilyl and dimethyl-tert.-butylsilyl.

Preferred aminoprotecting groups are acyl radicals of carbonic acid semiesters especially tert.-butoxycarbonyl or aryloxycarbonyl that is unsubstituted or substituted for example benzyloxycarbonyl or 4-nitrobenzyloxycarbonyl or diphenylmethoxycarbonyl or 2.2.2-trichloroethoxycarbonyl.

Other protected amino groups are sulphonated amino groups such as lower alkyl sulphonamides especially N-methyl sulphonamide and N-butylsulphonamide.

Hydroxy- and mercapto-protecting groups are for example acyl radicals such as lower alkanoyl which is unsubstituted or substituted for example with halogen, such as 2.2-dichloroacetyl or especially the acyl radicals or carboxylic acid semiesters mentioned in connection with the amino-protecting groups and also etherifying groups such as tert.-butyl or 2-oxa- or 2-thia-aliphatic hydrocarbon radicals, for example 1-methoxyethyl, 1-methyl-thiomethyl or 2-oxa- or 2-thia-cycloaliphatic hydrocarbon radicals, for example 2-tetrahydrofuryl or 2-tetrahydropyranyl or corresponding thia analogues and unsubstituted or substituted benzyl and diphenylmethyl. The phenyl radicals, can be substituted with halogen, lower alkoxy and/or nitro for example.

Hydroxy and mercapto groups may also be protected in the form of corresponding organic silyloxy or silylthio groups. Suitable silyl protecting groups are especially lower alkylsilyl such as trimethylsilyl or dimethyl-tert.-butylsilyl.

Two free functional groups may also be substituted by a common protecting group. Thus, for example hydroxy groups may be substituted by a methylene radical which is unsubstituted or preferably substituted for example with lower alkyl, such as methyl or aryl, such as phenyl or alkenyl such as methylene, isopropylidene, propylidene or benzylidene.

The substitutions on the radicals could also consist of a halogen especially fluorine, chlorine and iodine and further by a cyano group. The radicals could also be substituted with phosphorus containing radicals, such as phosphine, phosphinyl and phosDhonyl and with nitrogen containing radicals such as nitro or azido.

$R_{13}$ and $R_{14}$ are hydrogen, hydroxyl, acyl or substituted acyl, alkyl or substituted alkyl, aryl or substituted alkyl. The substitution on the substituted acyl, alkyl or aryl on the radical $R_{13}$ and $R_{14}$ can be hydroxy, oxo, alkoxy, aryloxy, halo, cyano, isocyanato, carboxy, esterified carboxy, amino, substituted amino, formyl, acyl, acyloxy, acylamino, sulfinyl, sulfonyl, phosphino, phosphinyl, phosphonyl, mercapto, alkylthio, arylthio, silyl, silyloxy, silylthio, nitro or azido.

In one preferred embodiment of the invention $R_{21}$, $R_{31}$ and $R_{42}$ are

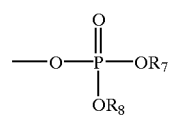

where $R_7$ and $R_8$ are as defined above $R_{22}$, $R_{32}$, $R_{41}$, $R_{61}$ and $R_{62}$ are hydrogen; $R_{11}$ and $R_{12}$ are different and are hydrogen, —$OR_9$ or —$NR_{13}R_{14}$ where $R_9$, and $R_{14}$ are as defined above and $R_{63}$ is —$OR_9$,

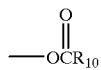

or —NR$_{13}$R$_{14}$ where R$_9$, R$_{10}$, R$_{13}$ and R$_{14}$ are as defined above.

Preferably R$_9$ and R$_{10}$ are
(1) alkyl or substituted alkyl such as methyl, ethyl, propyl, butyl, isobutyl, pentyl or hexyl or
(2) aryl or substituted aryl such as phenyl or biphenyl
and R$_{13}$ and R$_{14}$ are
(1) hydrogen
(2) lower alkyl or substituted alkyl such as methyl ethyl, propyl, butyl, isobutyl, pentyl or hexyl or
(3) lower acyl or substituted acyl such as acetyl or hydroxylated acetyl In one most preferred embodiment of this type of the invention R$_{21}$, R$_{31}$ and R$_{42}$ are

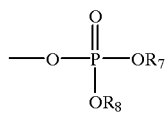

where R$_7$ and R$_8$ are hydrogen or a cation; R$_{22}$, R$_{32}$, R$_{41}$, R$_{61}$ and R$_{62}$ are hydrogen; R$_{11}$ and R$_{12}$ are different and are hydrogen or —OR$_9$ where R$_9$ is lower alkyl such as methyl, ethyl, propyl or butyl and R$_{63}$ is
(1) —OR$_9$ where R$_9$ is alkyl or substituted alkyl such as methyl, ethyl, propyl, butyl, pentyl, hexyl, silyl or substituted silyl or
(2)

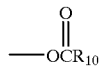

where R$_{10}$ is alkyl or substituted alkyl such as methyl, ethyl, propyl, butyl, pentyl, hexyl, aryl or substituted aryl such as phenyl.

In another preferred embodiment of the invention R$_{22}$, R$_{31}$ and R$_{42}$ are

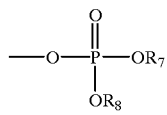

where R$_7$ and R$_8$ are as defined above
R$_{21}$, R$_{32}$, R$_{41}$, R$_{61}$, R62 are hydrogen; R$_{11}$ and R$_{12}$ are different and are hydrogen, —OR$_9$ or —NR$_{13}$R$_{14}$ where R$_9$, R$_{13}$ and R$_{14}$ are as defined above and R$_{63}$ is —OR$_9$,

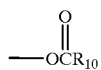

—NR$_{13}$R$_{14}$ where R$_9$, R$_{10}$, R$_{13}$ and R$_{14}$ are as defined above.

Preferably R$_9$ and R$_{10}$ are
(1) alkyl or substituted alkyl such as methyl, ethyl, propyl, butyl, isobutyl, pentyl, hexyl or
(2) aryl or substituted aryl such as phenyl or biphenyl.
and R$_{13}$ and R$_{14}$ are
(1) hydrogen
(2) lower alkyl or substituted alkyl such as methyl ethyl, propyl, butyl, isobutyl, pentyl, hexyl or
(3) lower acyl or substituted acyl such as acetyl or hydroxylated acetyl.

In still another preferred embodiment of the invention R$_{22}$, R$_{31}$ and R$_{41}$ are

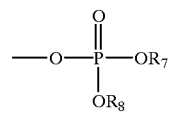

R$_{21}$, R32, R$_{42}$, R$_{61}$, R$_{62}$ are hydrogen; R$_{11}$ and R$_{12}$ are different and are hydrogen, —OR$_9$ or —NR$_{13}$R14 where R$_9$, R$_{13}$ and R$_{14}$ are as defined above and R$_{63}$ is —OR$_9$,

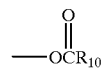

or —NR$_{13}$R$_{14}$ where R$_9$, R$_{10}$, R$_{13}$ and R$_{14}$ are as defined above.

Preferably R$_9$ and R$_{10}$ are
(1) alkyl or substituted alkyl such as methyl, ethyl, propyl, butyl, isobutyl, pentyl, hexyl or
(2) aryl or substituted aryl such as phenyl or biphenyl
and R$_{13}$ and R$_{14}$ are
(1) hydrogen
(2) lower alkyl or substituted alkyl such as methyl ethyl, propyl, butyl, isobutyl, pentyl, hexyl or
(3) lower acyl or substituted acyl such as acetyl or hydroxylated acetyl.

Other preferred embodiments of this invention are where R$_{21}$, R$_{32}$ and R$_{42}$ are

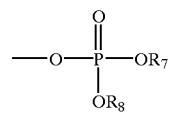

where P$_7$ and R$_8$ are as defined above
R$_{22}$, R$_{31}$, R$_{41}$, R$_{61}$ and R$_{62}$ are hydrogen; R$_{11}$ and R$_{12}$ are different and are hydrogen, —OR$_9$ or —NR$_{13}$R$_{14}$ where R$_9$, R$_{13}$ and R$_{14}$ are as defined above, and R$_{63}$ is —OR$_9$,

or —NR$_{13}$R$_{14}$ where R$_9$, R$_{10}$, R$_{13}$ and R$_{14}$ are as defined above.

Preferably R$_9$ and R$_{10}$ are
(1) alkyl or substituted alkyl such as methyl, ethyl, propyl, butyl, isobutyl, pentyl, hexyl or
(2) aryl or substituted aryl such as phenyl or biphenyl and $R_{13}$ and $R_{14}$ are
(1) hydrogen
(2) lower alkyl or substituted alkyl such as methyl ethyl, propyl, butyl, isobutyl, pentyl, hexyl or
(3) lower acyl or substituted acyl such as acetyl or hydroxylated acetyl.

In another preferred embodiment of this invention $R_{21}$, $R_{32}$ and $R_{41}$ are

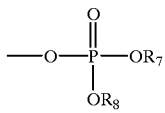

where $R_7$ and $R_8$ are as defined above
$R_{22}$, $R_{31}$, $R_{42}$, $R_{61}$ and $R_{62}$ are hydrogen; $R_{11}$ and $R_{12}$ are different and are hydrogen, —$OR_9$ or —$NR_{13}R_{14}$ and $R_{63}$ is —$OR_9$,

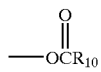

or —$NR_{13}R_{14}$ where $R_9$, $R_{10}$, $R_{13}$ and $R_{14}$ are as defined above.
Preferably $R_9$ and $R_{10}$ are
(1) alkyl or substituted alkyl such as methyl, ethyl, propyl, butyl, isobutyl, pentyl, hexyl or
(2) aryl or substituted aryl such as phenyl or biphenyl and $R_{13}$ and $R_{14}$ are
(1) hydrogen
(2) lower alkyl or substituted alkyl such as methyl ethyl, propyl, butyl, isobutyl, pentyl, hexyl or
(3) lower acyl or substituted acyl such as acetyl or hydroxylated acetyl.

In still another preferred embodiment of this invention $R_{21}$, R31 and $R_{41}$ are

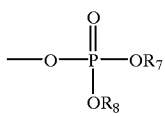

where $R_7$ and $R_8$ are as defined above
$R_{22}$, $R_{32}$, $R_{42}$, $R_{61}$ and $R_{62}$ are hydrogen; $R_{11}$ and $R_{12}$ are different and are hydrogen, —$OR_9$ or —$NR_3R_{14}$ and $R_{63}$ is —$OR_9$,

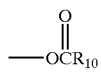

or —$NR_{13}R_{14}$ where $R_9$, $R_{10}$, 13 and $R_{14}$ are as define above.
Preferably $R_9$ and $R_{10}$ are
(1) alkyl or substituted alkyl such as methyl, ethyl, propyl, butyl, isobutyl, pentyl, hexyl or
(2) aryl or substituted aryl such as phenyl or biphenyl and $R_{13}$ and $R_{14}$ are
(1) hydrogen
(2) lower alkyl or substituted alkyl such as methyl, ethyl, propyl, butyl, isobutyl, pentyl, hexyl or
(3) lower acyl or substituted acyl such as acetyl or hydroxylated acetyl.

In one other preferred embodiment of this invention $R_{31}$, $R_{42}$ and $R_{63}$ are

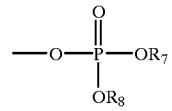

where $R_7$ and $R_8$ are as defined above
$R_{32}$, $R_{41}$, $R_{61}$, $R_{62}$ are hydrogen; $R_{11}/R_{12}$, $R_{21}/R_{22}$ are hydrogen, —$OR_9$ or —$NR_{13}R_{14}$ where $R_9$, $R_{13}$ and $R_{14}$ are as defined above.
Preferably $R_9$ is
(1) alkyl or substituted alkyl such as methyl, ethyl, propyl, butyl, isobutyl, pentyl, hexyl or
(2) aryl or substituted aryl such as phenyl or biphenyl and $R_{13}$ and $R_{14}$ are
(1) hydrogen
(2) lower alkyl or substituted alkyl such as methyl ethyl, propyl, butyl, isobutyl, pentyl, hexyl or
(3) lower acyl or substituted acyl such as acetyl or hydroxylated acetyl.

The different compounds according to this invention can be isolated in substantially pure form. Thus the different compounds can have a purity of 80–100%, such as 82–100% or 85–100%, preferable 90–100%.

The invention also relates to a pharmaceutical composition comprising as a pharmaceutically active ingredient one or more compounds of Formula (I).

The pharmaceutical composition can consist of a compound of Formula (I) solely or together with an additive, excipient or carrier.

It is suitable that the composition exists in unit dosage forms. The administration forms could be parenteral such as subcutaneous, intramuscular or intravenous or non-parenteral such as tablets, granules or capsules.

For administration to human patients appropriate dosages can routinely be determined by those, skilled in the art by extension of results obtained in animals. The preferred dosage for humans falls in within the range of 0.1 to 25 mg compound/day/kg body weight.

The composition usually contains 0.01–1.5 g, such as 0.05–1.3 g or preferably 0.1–1.0 g of a compound of Formula (I).

The compound of Formula (I) may be the only pharmaceutically active ingredient in the composition. However, also other pharmaceutically active ingredients can be present therein. The amount of the compound of Formula (I) should then constitute 5–95% or 15–80% such as 25–60% by weight of said active ingredients.

The following embodiment examples illustrate the invention however without limiting it thereto. Examples 1 to 3 illustrate the formation of the sodium salt of 1-O-methyl-6-O-(dimethyl-(1,1,2-trimethylpropyl)silyl)-α-D-mannopyranoside-2,3,4-trisphosphate. Example 4 shows the stability of the sodium salt of 1-O-methyl-6-O-butyl-α-D-mannopyranoside-2,3,4-trisphosphate against degradation compared to 1,5-anhydro-D-arabinitol-2,3,4-trisphosphate while example 5 demonstrates the manufacturing of a pharmaceutical composition for intravenous administration.

EXAMPLE 1

Dimethyl-(1,1,2-trimethylolpropyl)chlorosilane (11.2 ml) was added to a solution of 10.0 g methyl α-D- mannopyranoside in 51.5 ml pyridine in an ice bath. When the addition was completed, the ice bath was removed and the reaction mixture was left for 16 hours at room temperature. Methanol was added and the solvent was removed by evaporation. The residue was dissolved in ethyl acetate (200 ml), washed with a mixture of 10% hydrochloric acid and 10% aqueous ammonium sulfate (2×50 ml, 1:2), and saturated aqueous sodium hydrogen carbonate (40 ml). Drying with $Na_2SO_4$ was followed by removal of solvents and chromatography on a $SiO_2$-column with ethylacetate as an eluent, which gave 1-O-methyl-6-O-(dimethyl-(1,1,2-trimethylpropyl)silyl)-α-D-mannopyranoside.

EXAMPLE 2

1-O-Methyl-6-O-(dimethyl-(1,1,2-trimethylpropyl)silyl)-α-D-mannopyranoside (500 mg) was heated with bis(benzyloxy)diisopropylaminophosphine for 4 hrs at 60° C. TLC indicated conversion of the triol into the trisphosphate which was oxidized with m-chloroperbenzoic acid to give, after column chromatography, 1-O-methyl-6-O-(dimethyl-(1,1,2-tri-methylpropyl)silyl)-α-D-manno-pyranoside 2,3,4-tris(di-benzylphosphate)

EXAMPLE 3

1-O-Methyl-6-O-(dimethyl-(1,1,2-trimethylpropyl)silyl)-α-D-mannopyranoside 2,3,4-tris(dibenzylphosphate) (500 mg) was dissolved in ethanol containing 4 eauivalents of sodium acetate (10 ml). Palladium on charcoal (Pd/C, 100 mg) was added and the mixture was hydrogenated with stirring. After 24 hours the solvent was removed to give the sodium salt of 1-O-methyl 6-O-(dimethyl-(1,1,2-trimethylpropyl)-silyl)-α-D-mannopyranoside-2,3,4-trisphosphate.

EXAMPLE 4

The stability against phosphatase degradation was assayed by using alkaline phosphalase from bovine intestinal mucosa (Sigma) with a concentration of 1 Unit/ml in a 0,1M Tris HCl-buffer comprsing 0.1 mM $MgCl_2$ and 0.1 mM. Zn $Cl_2$ at pH 7.0. To 10 ml of the buffer was added 5 mg of 1.5 anhydro-D-arabnitol-2,3,4-trisphosphate (Cmpd 1) to a final concentration of 5 mmol phosporus/1.

To another aliquot of 10 ml buffer was added equimolar concentration of 1-O-metyl-6-O-butyl-a-D-mannopyranoside-2,3,4-trisphosphate (Cmpd 2). The temperature was raised to 37° C. and the stability of the compounds was followed by the determination of free phosphorus in the solutions. Samples were analyzed every hour for six hours and the following results were obtained. Compound 1 was outside while compound was 2 was inside the scope of the invention.

| | Free phosphorus/total phosporus % | |
|---|---|---|
| Time (hrs) | Cmpd 1 (outside the invention) | Cmpd 2 (according to the invention) |
| 0 | 0 | 0 |
| 1 | 15.5 | 2.1 |
| 2 | 29.9 | 3.0 |
| 3 | 43.3 | 3.7 |
| 4 | 55.8 | 4.7 |
| 5 | 75.6 | 5.8 |
| 6 | 85.5 | 6.0 |

These results show that the liberation of phosphorus from compound 2 (1-O-methyl-6-O-butyl-α-D-mannopyranoside-2,3,4-phosphate) is very slow. Thus the compound 2 is very stable against degradation. There is a rather quick liberation of phosphorus from compound 1, which means that it is not stable against degradation.

EXAMPLE 5

0.5 g of the sodium salt of 1-O-methyl-6-O-butyl-α-D-mannopyranoside-2,3,4-trisphosphate and 0.77 g sodium chloride we-re dissolved in 98.73 ml of water for injection to form a solution suitable for injection into a person or an animal.

What is claimed is:

1. A pharmaceutical composition comprising as a pharmaceutically active ingredient a compound according to formula I

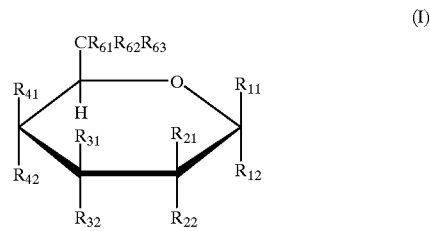

(I)

and a pharmaceutically acceptable carrier, excipient or additive thereof;

where $R_{21}$, $R_{31}$ and $R_{42}$ are

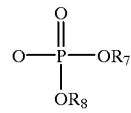

where $R_7$ and $R_8$ independently are
(1) hydrogen;
(2) a cation selected from the group consisting of sodium, potassiumn and calcium; or in the case where the cation is $Ca^{+2}$, $R_7$ and $R_8$ jointly represent the cation;
(3) a lower alkyl selected from the group consisting of methyl, ethyl, propyl, butyl, pentyl; were $R_{22}$, $R_{32}$, $R_{41}$, $R_{61}$ and $R_{62}$ are hydrogen where one of $R_{11}$ and $R_{12}$ is hydrogen, and the other is selected from
(1) —$OR_9$;

(2)

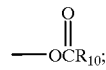

or
(3) —$NR_{13}R_{14}$
and where $R_{63}$ is
(1) $OR_9$;

(2)

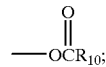

or (3) —NR$_{13}$R$_{14}$,
where R$_9$ is
  (a) straight or branched alkyl with 1 to 24 carbon atoms;
  (b) cycloalkyl with 3 to 16 carbon atoms;
  (c) alkenyl with 2 to 24 carbon atoms;
  (d) cycloalkenyl with 4 to 16 carbon atoms;
  (e) aryl with 6 to 24 carbon atoms;
  (f) aralkyl;
  (g) alkaryl;
  (h) aralkenyl;
  (i) alkenylaryl;
  (j) a heterocyclic group with at least one atom of oxygen, nitrogen or sulfur;
  (k) a glycosyl residue;
  (l) a glyropeptide;
  (m) a glycoprotein;
  (n) a glycolipid;
  (o) carboxy, sulfonyl or phosphonyl;
  (p) silyl or substituted silyl; or
  (q) hydrogen;
    wherein the above groups (a) to (n) are unsubstituted or substituted with hydroxy, oxo, alkoxy, aryloxy, halocyano, isocyanato, carboxy, esterifed carboxy, amino, substituted amino, formyl, acyl, acyloxo, acylamino, sulfinyl, sulfonyl, phosphino, phosphinyl, phosphonyl, mercapto, alkylthio, arylthio, silyl, silyloxy, silylthio, nitro or azido;
where R$_{10}$ is
  (a) straight or branched alkyl with 1 to 24 carbon atoms;
  (b) cycloalkyl with 3 to 16 carbon atoms;
  (c) alkenyl with 2 to 24 carbon atoms;
  (d) cycloalkenyl with 4 to 16 carbon atoms;
  (e) aryl with 6 to 24 carbon atoms;
  (f) aralkyl;
  (g) alkaryl;
  (h) aralkenyl;
  (i) alkenylaryl;
  (j) a heterocyclic group with at least one atom of oxygen, nitrogen or sulfur;
  (k) carboxy or esterified carboxy;
  (l) amino or substituted amino; or
  (m) hydrogen,
    wherein the above groups (a) to (i) are unsubstituted or substituted with hydroxy, oxo, alkoxy, aryloxy, halocyano, isocyanato, carboxy, esterfied carboxy, amino, substituted amino, formyl, acyl, acyloxo, acylamino, sulfinyl, sulfonyl, phosphino, phospinyl, phosphonyl, mercapto, alkylthio, arylthio, silyl, silyloxy, silylthio, nilro or azido;
and where R$_{13}$ and R$_{14}$ are
  (a) hydrogen;
  (b) hydroxyl;
  (c) lower acyl selected from the group consisting of formyl, acetyl, propionyl, butyryl, valeryl, pivaloyl; or
  (d) lower alkyl selected from the group consisting of methyl, ethyl, propyl, butyl, pentyl or hexyl.

2. The pharmaceutical composition according to claim 1 where R$_{21}$, R$_{31}$ and R$_{42}$ are

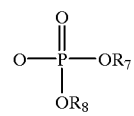

where R$_7$ and R$_8$ are
  (1) hydrogen;
  (2) a cation selected from the group consisting of sodium, potassium or calcium, where R$_{22}$, R$_{32}$, and R$_{41}$ are hydrogen, where R$_{11}$ and R$_{12}$ are different and one is hydrogen, and the other is —OR$_9$,
and where R$_{63}$ is
  (1) hydrogen;
  (2) —OR$_9$; or

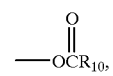
(3)

where R$_9$ and R$_{10}$ independently are
  (1) alkyl or substituted alkyl selected from the group consisting of methyl, ethyl, propyl, butyl, isobutyl, pentyl or hexyl;
  (2) aryl or substituted aryl selected from the group consisting of phenyl or biphenyl or
  (3) silyl or substituted silyl.

3. A pharmaceutical composition according to claim 1, where R$_{21}$, and R$_{31}$ and R$_{43}$ are

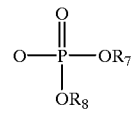

where R$_7$ and R$_8$ independently are
  (1) hydrogen;
  (2) a cation selected from the group consisting of sodium, potassium and calcium
where, R$_{22}$, R$_{32}$, R$_{41}$, R$_{61}$, R$_{62}$ are hydrogen;
where one of R$_{11}$ and R$_{12}$ independently is hydrogen, and the other is —OR$_9$,
and where R$_{63}$ is
  (1) —OR$_9$; or

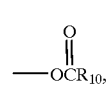
(2)

where R$_9$ and R$_{10}$ indpendently are
  (a) alkyl or substituted alkyl selected from the group consisting of methyl, ethyl, propyl, butyl, isobutyl, pentyl or hexyl;
  (b) aryl or substituted aryl selected from the group consisting of phenyl or biphenyl; or
  (c) silyl or substituted silyl.

4. A pharmaceutical composition comprising as a pharmaceutically active ingredient a compound according to formula I (I)

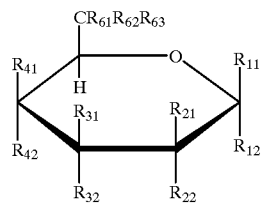

and a pharmaceutically acceptable carrier, excipient or additive thereof;

where $R_{22}$, $R_{31}$ and $R_{42}$ are

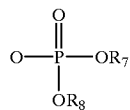

where $R_7$ and $R_8$ independently are
(1) hydrogen;
(2) a cation selected from the group consisting of sodium, potassium and calcium; or in the case where the cation is $Ca^{+2}$, $R_7$ and $R_8$ jointly represent the cation;

where $R_{21}$, $R_{32}$, $R_{41}$ are hydrogen; where $R_{11}$ and $R_2$ are different and one is hydrogen, and the other is —$OR_9$, and where $R_{63}$ is
(1) hydrogen;
(2) —$OR_9$; or (3)

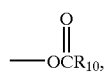

where $R_9$ and $R_{10}$ independently are
(1) alkyl or substituted alkyl selected from the group consisting of methyl, ethyl, propyl, butyl, isobutyl, pentyl or hexyl;
(2) aryl or substitutted aryl selected from the group consistinng of phenyl or biphenyl; or
(3) silyl or substituted silyl.

5. A pharmaceutical composition comprising as a pharmaceutically active ingredient a compound according to formula I (I)

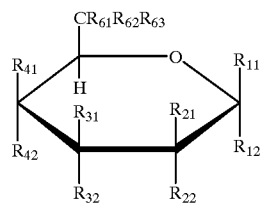

and a pharmaceuticaly acceptable carrier, excipient or additive thereof;

where $R_{21}$, $R_{32}$ and $R_{42}$ are

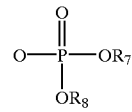

where $R_7$ and $R_8$ independently are
(1) hydrogen;
(2) a cation selected from the group consisting of sodium, potassium and calcium; or in the case where the cation is $Ca^{+2}$, $R_7$ and $R_8$ jointly represent the cation;
(3) a lower alkyl selected from the group consisting of methyl, ethyl, propyl, butyl, pentyl where $P_{22}$, $R_{32}$, $R_{41}$ are hydrogen;

where $R_{11}$ and $R_{12}$ are different and one is hydrogen, and the other is —$OR_9$
and where $R_{63}$ is
(1) hydrogen;
(2) —$OR_9$; or (3)

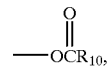

where $R_9$ and $R_{10}$ independently are
(1) alkyl or substituted alkyl selected from the group consisting of methyl, ethyl, propyl, butyl, isobutyl, pentyl or hexyl;
(2) aryl or substituted aryl selected from the group consisting of phenyl or biphenyl or
(3) silyl or substituted silyl.

6. A pharmaceutical composition comprising as a pharmaceutically active ingredient a compound according to formula I (I)

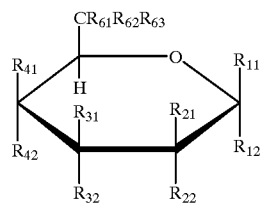

and a pharmaceutically acceptable carrier, excipicnt or additive thereof;

where $R_{21}$, $R_{32}$ and $R_{41}$ are

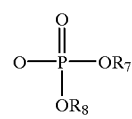

where $R_7$ and $R_8$ are
(1) hydrogen;
(2) a cation selected from the group consisting of sodium, potassium and calcium; where $R_{22}$, $R_{31}$, and $R_{42}$ are hydrogen; where $R_{11}$ and $R_{12}$ are different and one is hydrogen, and the other is —$OR_9$, and where $R_{63}$ is
(1) hydrogen;
(2) —$OR_9$; or (3)

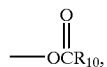

where $R_9$ and $R_{10}$ independently are
(1) alkyl or substituted alkyl selected from the group consisting of methyl, ethyl, propyl, butyl, isobutyl, pentyl, hexyl;
(2) aryl or substituted aryl selected from the group consisting of phenyl or biphenyl or
(3) silyl or substituted silyl.

7. A pharmaceutical composition comprising as a pharmaceutically active ingredient a conpound according to formula I (I)

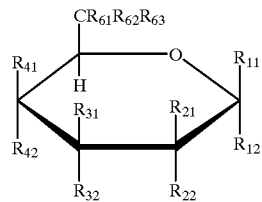

and a pharmaceutically acceptable carrer, excipient or additive thereof;

where $R_{21}$, $R_{31}$ and $R_{41}$ are

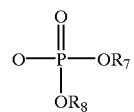

where $R_7$ and $R_8$ are
(1) hydrogen;
(2) a cation selected from the group consisting of sodium, potassium or calcium, where $R_{22}$, $R_{32}$, and $R_{42}$ are hydrogen; where $R_{11}$ and $R_{12}$ are different and one is hydrogen, and the other is —$OR_9$, and where $R_{63}$ is
(1) —$OR_9$; or (2)

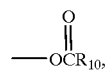

where $R_9$ and $R_{10}$ independently are
(1) alkyl or substituted alkyl selected from the group consisting of methyl, ethyl, propyl, butyl, isobutyl, penityl or hexyl;
(2) aryl or substited aryl selected from the group consisting of phenyl or biphenyl; or
(3) silyl or substituted silyl.

* * * * *